(12) United States Patent
Johnson

(10) Patent No.: US 8,940,342 B1
(45) Date of Patent: Jan. 27, 2015

(54) COSMETIC COMPOSITION HAVING POMACE OLIVE OIL

(71) Applicant: Pamela A Johnson, Rock Hill, SC (US)

(72) Inventor: Pamela A Johnson, Rock Hill, SC (US)

( * ) Notice: Subject to any disclaimer, the term of this patent is extended or adjusted under 35 U.S.C. 154(b) by 0 days.

(21) Appl. No.: 14/166,165

(22) Filed: Jan. 28, 2014

Related U.S. Application Data

(63) Continuation of application No. 12/931,900, filed on Feb. 14, 2011, now Pat. No. 8,663,710, which is a continuation of application No. 12/658,958, filed on Feb. 18, 2010, now Pat. No. 7,887,857, which is a continuation of application No. 11/986,143, filed on Nov. 20, 2007, now abandoned.

(51) Int. Cl.
| | | |
|---|---|---|
| *A01N 65/00* | (2009.01) | |
| *A61K 8/92* | (2006.01) | |
| *A61K 8/98* | (2006.01) | |
| *A61Q 19/00* | (2006.01) | |
| *A61Q 5/06* | (2006.01) | |
| *A61Q 5/12* | (2006.01) | |

(52) U.S. Cl.
CPC .................. *A61K 8/922* (2013.01); *A61K 8/927* (2013.01); *A61K 8/982* (2013.01); *A61K 8/986* (2013.01); *A61Q 19/00* (2013.01); *A61Q 5/06* (2013.01); *A61Q 5/12* (2013.01)
USPC ........................................................ 424/725

(58) Field of Classification Search
None
See application file for complete search history.

(56) References Cited

U.S. PATENT DOCUMENTS

| | | |
|---|---|---|
| 3,934,003 A | 1/1976 | Tuma et al. |
| 6,113,971 A | 9/2000 | Elmaleh |
| 6,187,318 B1 | 2/2001 | Mitchell et al. |
| 7,195,770 B2 | 3/2007 | Gitomer et al. |
| 7,205,012 B1 | 4/2007 | Hill |

FOREIGN PATENT DOCUMENTS

| | | |
|---|---|---|
| WO | WO-2007086613 A1 | 8/2007 |
| WO | WO-2007112579 A1 | 10/2007 |

OTHER PUBLICATIONS

United States Patent and Trademark Office; Office Action Summary for U.S. Appl. No. 11/986,143; published Oct. 19, 2009, pp. 1-11; Alexandria, Virginia, USA; (11 pages).
United States Patent and Trademark Office; Office Action Summary for U.S. Appl. No. 11/986,143; published Apr. 7, 2009; pp. 1-4; Alexandria, Virginia, USA; (4 pages).
United States Patent and Trademark Office; Office Action Summary for U.S. Appl. No. 12/658,956; published Sep. 7, 2010; pp. 1-5; Alexandria, Virginia, USA (5 pages).

*Primary Examiner* — Michael Meller
(74) *Attorney, Agent, or Firm* — Neal P. Pierotti; Metz Lewis Brodman Must O'Keefe

(57) ABSTRACT

A cosmetic composition is provided. The cosmetic composition may include pomace olive oil and a first moisturizing oil. The first moisturizing oil may be safflower oil, mango butter, or hemp seed oil. A second oil can also be included and may be coconut oil or grape seed oil. A bacterial control oil can also be present and may be sweet orange oil or lemongrass oil.

4 Claims, No Drawings

COSMETIC COMPOSITION HAVING POMACE OLIVE OIL

RELATED APPLICATIONS

The present application is a continuation and claims the benefit of U.S. application Ser. No. 12/931,900 filed on Feb. 14, 2011 and entitled "Cosmetic Composition Having Pomace Olive Oil" the entire contents of which are incorporated by reference herein in their entirety for all purposes. U.S. application Ser. No. 12/931,900 is a continuation and claims the benefit and priority of U.S. application Ser. No. 12/658,958 filed on Feb. 18, 2010 that issued as U.S. Pat. No. 7,887,857 B1 on Feb. 15, 2011 and entitled, "Cosmetic Composition Having Pomace Olive Oil" the entire contents of which are also incorporated by reference herein in their entirety for all purposes. U.S. Pat. No. 7,887,857 B1 is a continuation and claims the benefit and priority of U.S. application Ser. No. 11/986,143 filed on Nov. 20, 2007 and entitled, "Cosmetic Composition Having Pomace Olive Oil" and now abandoned. The present application also claims priority to and the benefit of U.S. application Ser. No. 11/986,143 the entire contents of which are also incorporated by reference herein in their entirety for all purposes.

FIELD OF THE INVENTION

The present invention relates generally to cosmetic compositions. More particularly, the present application involves cosmetic compositions that contain olive oil and that can be applied to the skin and/or hair of a user.

BACKGROUND

Cosmetic compositions are known for enhancing the look, feel and health of a user. One such cosmetic composition is shampoo which is used to remove oils, dirt, skin particles and other contaminants from the hair and scalp of a user. Shampoo is generally applied in conjunction with water to achieve the desired contaminant removal and cleaning effect. After cleaning, the hair of a user may be further conditioned to achieve a desired look. For example, pomade can be applied to the hair of a user in order to style the hair to a particular, desired form. Pomade is generally greasy or waxy in feel and typically imparts these properties into the hair of the user once applied. Pomade is usually of such a consistency that it cannot readily be combed out of the hair of the user but may only be removed upon washing with water.

Additional cosmetic compositions include skin creams and emulsions that are applied to the skin of the user. Typical application spots include the face and hands of the user, although any skin of the user may be treated with these compositions. Skin creams and emulsions seek to improve the softness of the skin and prevent it from drying out during times of cold, dry weather. Further, skin application products are commonly used for the prevention of acne and to aid in the healing of cuts or burns on the skin of the user.

Cosmetic compositions are common in everyday life and are generally used on a daily basis by many individuals. Particular needs are thus present for cosmetic compositions made from certain components for use in imparting various desired benefits to the skin and hair of a user.

SUMMARY

Various features and advantages of the invention will be set forth in part in the following description, or may be obvious from the description, or may be learned from practice of the invention.

One aspect of one exemplary embodiment includes a cosmetic composition that has pomace olive oil and a first moisturizing oil. The first moisturizing oil may be safflower oil, mango butter, or hemp seed oil. A second oil can also be included and may be coconut oil or grape seed oil. A bacterial control oil can also be present and may be sweet orange oil or lemongrass oil.

Another aspect of an additional embodiment resides in a cosmetic composition as immediately mentioned that further includes a first absorption oil. The first absorption oil can be sweet almond oil, apricot kernel oil, or jojoba oil.

One additional aspect of a further embodiment is found in a cosmetic composition as previously mentioned that further includes a vitamin rich oil. The vitamin rich oil can be sunflower oil, avocado oil, or sesame oil.

Yet another aspect of another embodiment is found in a cosmetic composition as previously mentioned that further has a texturing agent. The texturing agent can be palm kernel oil or palm kernel flakes.

Another aspect of an additional exemplary embodiment resides in a cosmetic composition as previously discussed that further includes a first butter. The first butter can be aloe butter, cocoa butter, shea butter, or lanolin butter.

Still another additional aspect of a further embodiment resides in a cosmetic composition that has both pomace olive oil and safflower oil. An additional oil is also present. The additional oil can be coconut oil, sweet almond oil, or grape seed oil.

Another additional aspect of a further embodiment includes a cosmetic composition as immediately mentioned that further includes sweet orange oil.

Also provided in accordance with one aspect of another embodiment is a cosmetic composition as previously discussed in which the additional oil is sweet almond oil. The composition further includes rosemary oleoresin extract and tea tree oil.

Another aspect exists in a cosmetic composition that has olive oil and a first oil. The first oil is safflower oil, mango butter, hemp seed oil, sweet almond oil, jojoba oil, apricot oil, or palm kernel oil. A second oil is present and is coconut oil, grape seed oil, sunflower oil, sesame oil, avocado oil, tea tree oil, or shea oil.

A further aspect includes a cosmetic composition as immediately discussed that further includes a third oil. The third oil is sweet orange oil, lemongrass oil, lemon oil, ylang-ylang oil, or clary-sage oil.

These and other features, aspects and advantages of the present invention will become better understood with reference to the following description and appended claims.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a cosmetic composition that can be applied to the body of a user. For example, the cosmetic composition may be configured as a moisturizing shampoo and applied to the hair of a user. Alternatively, the cosmetic composition can be configured as a hair and body oil that is capable of being applied to both the hair and skin of the user. Another arrangement of the cosmetic composition is found in a pomade that can be used in the styling of the hair of an individual. A further configuration exists in arranging the cosmetic composition as a dry skin emulsion for application to the skin of a user to enhance its look and feel. The cosmetic composition may include, in accordance with one exemplary embodiment, pomace olive oil that when applied to the skin can provide moisturizing properties. Additional components may be included in the cosmetic composition in order to achieve various beneficial results when applied to the body of a user. In certain embodiments all of the components of the cosmetic composition are natural components.

The cosmetic composition can be provided with a number of different components in varying quantities in order to achieve a desired result. By way of example, the cosmetic composition may be provided as a dry skin emulsion capable of being applied to the skin of a user in order to increase skin moisture, look, and/or softness. One such exemplary embodiment of the cosmetic composition is provided as shown in Table 1.

TABLE 1

| Component | Percentage by volume |
|---|---|
| Pomace Olive Oil | 18.0% |
| Sweet Almond Oil | 9.0% |
| Jojoba Oil | 9.0% |
| Mango Butter | 9.0% |
| Aloe Butter | 9.0% |
| Cocoa Butter | 9.0% |
| Shea Butter | 9.0% |
| Coconut Oil | 9.0% |
| Palm Kernal Flakes | 9.0% |
| Beeswax | 5.0% |
| Lanolin Butter | 2.5% |
| Petroleum Jelly | 2.5% |
| Sweet Orange Oil | 0.05% |
| Lemon Oil | 0.05% |

In addition, an optional fragrance can be added such as vanilla fragrance oil. The volume of the resulting composition may be 0.05% vanilla fragrance oil when added. Again, it is to be understood that the aforementioned components and volumes disclosed in Table 1 are only exemplary and that various arrangements are possible in accordance with other exemplary embodiments of the cosmetic composition. For example, certain components such as aloe butter, cocoa butter, and jojoba oil may be completely removed from the cosmetic composition or may be replaced with other components in varying amounts in accordance with other arrangements. The dry skin emulsion illustrated in Table 1 can have a total volume of approximately 44 ounces, although it is to be understood that the cosmetic composition can be provided in a variety of volumes in other embodiments. Addition of the volumes by percentages in Table 1 adds up to 100.1%. It is to be understood that as presented herein, there is an error factor of ±2% regarding the volumes listed for the individual components of the cosmetic composition, and as such the tabulated totals of volumes may be from 98% to 102%.

Pomace olive oil is a fruit oil obtained from olives. Olive oil can be obtained through the pressing of olives. The portion of the olive that remains after pressing is sometimes referred to as pomace. Solvents or other physical treatments may be used on the pomace to produce an oil known as pomace olive oil. Heat and/or hexane may be used in certain instances in drawing the pomace olive oil from the pomace. In some instances, pomace olive oil may be obtained through exclusion of oils obtained by re-esterification and of any mixture with other types of oils. In certain instances, pomace olive oil may be a blend of the refined pomace olive oil and virgin olive oil (oil obtained directly from the olive such as through mechanical processes). Pomace olive oil may have a free acidity of up to 1 gram per 100 grams.

The pomace olive oil employed may be cosmetic grade olive oil. The pomace olive oil can have a moisturizing effect on the skin and hair, and may act to aid in the regeneration of skin cells when applied thereon. When applied to the hair of a user, the pomace olive oil functions to soften the hair and increase shine. The pomace olive oil may be the carrier oil of the cosmetic composition in accordance with various exemplary embodiments. In accordance with other arrangements, the pomace olive oil may be present from 7.2% to 20% by volume in the cosmetic composition.

Although disclosed as being pomace olive oil, this component may be substituted with virgin olive oil and/or extra virgin olive oil in accordance with other exemplary embodiments. Further, other arrangements exist in which pomace olive oil, virgin olive oil, and extra virgin olive oil are all present in the cosmetic composition.

The cosmetic composition may also include sweet almond oil. This oil is obtained from the dried kernel of the almond plant. Sweet almond oil is protein rich and helps itchy or inflamed areas of the skin when applied thereto. Sweet almond oil also acts as a moisturizer when applied to the body of the user in the cosmetic composition. Additionally, sweet almond oil functions as an absorption oil as it assists in absorption into the skin of various components of the cosmetic composition. Sweet almond oil may also act to soften the skin and hair of the user when applied.

Another component of the cosmetic composition, as shown in Table 1, is jojoba oil. Jojoba oil is the liquid wax produced in the seed of the jojoba plant and can be utilized in the composition to aid in absorption of the various components into the skin of the user. Jojoba oil is similar in make up to human sebum which may account for its absorption properties. Additionally, jojoba oil may be beneficial in the cosmetic composition as it aids in the healing process of skin.

Mango butter may also be included in the cosmetic composition. Mango butter can be made through extraction of the de-shelled fruit kernels of mango trees. Mango butter can provide moisturizing benefits to the skin of the user and may minimize itching of the skin. Mango butter is an exotic oil that has a buttery feel at body temperature. As such, it is to be understood that as used herein, the term mango butter is broad enough to cover substances that are known as mango butter or are known as mango oil.

Aloe vera butter also forms a portion of the cosmetic composition shown in Table 1. The aloe vera butter may be formed, for example, through extraction of aloe vera using fatty coconut oil. The aloe vera butter as provided may impart anti aging benefits, anti inflammatory benefits, and pain relief to the user when applied. Also, the aloe vera butter can function to reduce the presence of acne on the skin of the user.

Cocoa butter can also be used in the cosmetic composition. Cocoa butter is extracted from cacao beans. Cocoa butter can provide numerous benefits to the cosmetic composition. For example, the cocoa butter can function to improve the texture of the cosmetic composition and may be of a desirable fragrance. Additionally, cocoa butter functions as an absorption agent to increase the absorption of various components of the cosmetic composition into the skin and hair of the user.

The cosmetic composition shown in Table 1 also includes shea butter. Shea butter may be extracted from the fruit of the shea tree by crushing and/or boiling. Shea butter may be advantageous in the cosmetic composition for imparting moisturizing and absorption properties.

Coconut oil may also be included in the cosmetic composition. This oil is formed through extraction from dried coconut. Coconut oil functions as a moisturizing agent when incorporated into the cosmetic composition. Additionally, the coconut oil can improve the luster of hair when the cosmetic composition is used thereon.

Palm kernel flakes can also be included in the cosmetic composition as shown in the exemplary embodiment in Table 1. The palm kernel flakes improve texture of the cosmetic composition and aid in moisturizing.

Beeswax may also be present in the cosmetic composition and is made in the bee hives of honey bees. Beeswax may provide a softening feel to the cosmetic composition. Additionally, the beeswax may function as a thickening agent to effect the texture of the cosmetic composition, and this component can act as a moisturizer to the skin when applied. Beeswax may also act as a humectant in the cosmetic composition.

Another component of the cosmetic composition shown in Table 1 is lanolin butter. Lanolin butter is made from wool and has a high lipid content. Lanolin butter is easily absorbed into and contributes to high hydration levels of the skin.

An additional component of the cosmetic composition may be petroleum jelly. This component is hydrophobic and repels water therefrom. This component has a sealing effect when placed onto the skin of a user and prevents moisture from escaping, thus attributing a moisturizing effect. Petroleum jelly can also aid in accelerating the rate of skin healing by preventing bacteria from infecting cuts or burns on damaged skin.

Sweet orange oil is also present in the cosmetic composition shown in Table 1. Sweet orange oil is produced by glands inside the rind of an orange. This oil can be extracted through a process in which the outer layer of the rind is rasped away from the rest of the orange and placed into a centrifuge. The sweet orange oil can be forced from the cell walls through the application of pressure applied by the centrifuge. Sweet orange oil acts as a bacterial control oil in that it prevents or inhibits the growth of bacteria in the cosmetic composition.

Lemon oil is another component of the described cosmetic composition. This oil is similar to sweet orange oil in that it is present within the rind of the fruit. The lemon peel may be cold pressed in order to extract the lemon oil therefrom. Lemon oil is beneficial in that it functions as a bacterial control oil to prevent bacteria from forming or growing in the cosmetic composition in order to maintain its shelf life and effectiveness. Lemon oil when applied to the hair of the user is also capable of stripping the hair of build-up.

The cosmetic composition shown in Table 1 may optionally include 0.05% by volume of vanilla fragrance oil. The vanilla fragrance oil can be included in order to enhance the aroma of the cosmetic compound. This oil is obtained from cured vanilla pods and has a vanilla aroma. Other components may be added to the cosmetic composition in order to achieve a different resulting fragrance.

When provided as a skin emulsion, the cosmetic composition was discovered to achieve an unexpected benefit of being readily absorbed into the skin of the user. In certain instances, the cosmetic composition was absorbed into the skin within 5 minutes of application such that it was no longer present on the surface of the skin.

In accordance with another exemplary embodiment of the present invention, the cosmetic composition can be formulated as a moisturizing shampoo. The cosmetic composition is capable of being absorbed into the open follicles of a user's hair in order to restore luster thereto. The cosmetic product has been found to protect the hair of a user during heat styling. Additionally, application of the cosmetic composition results in hair that is both soft and shiny after being blow dry. One embodiment of the cosmetic composition when formulated and used as a moisturizing shampoo is provided with reference to Table 2 below.

TABLE 2

| Component | Percentage by Volume |
|---|---|
| Clear Shampoo Base | 65.0% |
| Pomace Olive Oil | 7.5% |
| Coconut Oil | 7.5% |
| Corn Starch-based Rheology Modifier and Emulsion Stabilizer | 7.5% |
| Jojoba Oil | 3.8% |
| Avocado Oil | 3.8% |
| Functional Honey | 3.8% |
| Tea Tree Oil | 0.08% |
| Hemp Seed Oil | 0.08% |
| Shea Oil | 0.08% |
| Peppermint Oil | 0.08% |
| Rosemary Oleoresin Extract | 0.05% |
| Lemongrass Oil | 0.05% |
| Ylang-ylang Oil | 0.05% |
| Clary-Sage Oil | 0.05% |

In addition, an optional fragrance can be added such as vanilla fragrance oil. The volume of the resulting composition may be 0.05% vanilla fragrance oil when added. Again, it is to be understood that the aforementioned components and volumes disclosed in Table 2 are only exemplary and that various arrangements are possible in accordance with other exemplary embodiments of the cosmetic composition. The moisturizing shampoo illustrated in Table 2 can have a total volume of approximately 28 ounces, although it is to be understood that the cosmetic composition can be provided in a variety of volumes in other embodiments.

The cosmetic composition illustrated in Table 2 includes a clear shampoo base. This component may be obtained, for instance, from New Directions Aromatics, Inc. having offices at 21B Regan Road, Brampton, Ontario, L7A 1C5. The clear shampoo base is a clear, viscous liquid that is capable of being combined with oils in order to form a desired moisturizing shampoo. The clear shampoo base includes water, sodium laureth sulfate, cocamide DEA, cocamidopropyl betaine, and sodium chloride as its main ingredients.

Also included is a corn starch-based rheology modifier and emulsion stabilizer. This component may be, for instance, STRUCTURE® XL, which is produced by National Starch Personal Care having offices at 6203 Sempach-Station, Switzerland. This component is naturally derived and increases emulsion stability in the cosmetic composition. Aside from aiding in emulsion stabilization, the component provides aesthetic enhancement and viscosity build.

The cosmetic composition also includes avocado oil. This oil is extracted from the avocado. This component provides regenerative and moisturizing properties. Avocado oil is rich in vitamins B1, B2, A and E and can function to impart these vitamins to the user when incorporated into the cosmetic composition.

Functional honey is also present in the cosmetic composition illustrated in Table 2. This component is sometimes known as honeyquat. Functional honey is capable of destroying or inhibiting the formation of bacteria and is a natural anti-oxidant and is high in vitamin C. When applied to the skin, this component is capable of promoting collagen formation and can cleanse the skin while improving skin texture and surface smoothness. When used on the hair, functional honey can provide increased hair shine.

Tea tree oil is also present in the cosmetic composition. This component may be obtained from the leaves of the melaleuca alternifolia plant. Tea tree oil is capable of controlling dandruff when the cosmetic composition is applied as a moisturizing shampoo. Additionally, this component may provide antiseptic properties and is beneficial in the treatment of acne and minor wounds.

Hemp seed oil is also included. This component is obtained through the seed of the hemp plant. Hemp seed oil can contribute anti-aging and moisturizing properties to the cosmetic component when applied to the skin of the user. Also, incorporation in the moisturizing shampoo in Table 2 is beneficial as this component increases hair manageability. Hemp seed oil can also provide relief from dry scalp and hair damage due to heat styling and chemical treatments.

An additional component of the cosmetic composition shown in Table 2 is shea oil which is obtained as a by-product of shea butter production from the seed. Shea oil may be advantageous in the cosmetic composition for imparting moisturizing and absorption properties.

Peppermint oil is also included in the moisturizing shampoo. This component is advantageous in that it stimulates the scalp and promotes hair growth.

An additional component of the cosmetic composition of Table 2 is rosemary oleoresin extract. This component is high in amino acids that function to maintain hair health. Rosemary oleoresin extract may also be useful in that it may act to prevent the cosmetic composition from becoming discolored. For example the presence of the rosemary oleoresin extract may function to prevent the resulting cosmetic composition from becoming dark in color.

Lemongrass oil is also included in the cosmetic composition. This oil is obtained from cymbopogon grasses. The main component of lemongrass oil is citral which makes up approximately four fifths of its total. Lemongrass oil is an anti-bacterial oil in that it kills or inhibits the growth of bacteria in the cosmetic composition. Application to the hair of a user is also beneficial in that the lemongrass oil strips the hair of build-up.

Another component of the cosmetic composition shown in Table 2 is ylang-ylang oil which is obtained from the flower of the cananga tree. This oil is generally obtained through steam distillation of the flower. Application to the skin of ylang-ylang oil may be beneficial in that it is known to normalize sebum secretion. Additionally, application to the hair of a user of ylang-ylang oil may be beneficial in that it provides protection to the hair from split ends.

Clary-sage oil is usually obtained through distillation from the salvia sclarea plant. This component improves the luster of hair when applied thereon. Also, clary-sage oil, when incorporated into a moisturizing shampoo, can coat the shaft of the hair to afford protection thereto.

Additional components such as the pomace olive oil, coconut oil, and jojoba oil may be incorporated to impart, among other properties, increased hair luster upon application of the cosmetic composition. Other properties and benefits of these components are as described above. It is to be understood that the presented components and volumes are only exemplary and that other components may be added, subtracted, or substituted from the cosmetic composition when arranged as a moisturizing shampoo. Additionally, the percentages by volume may be varied from those disclosed in Table 2.

In accordance with another exemplary embodiment of the present invention, the cosmetic composition can be formulated as a hair and body soothing oil. The cosmetic composition can be applied to both the hair and skin of the user in order to impart various benefits thereon. One embodiment of the cosmetic composition when formulated and used as a hair and body soothing oil is provided with reference to Table 3 below.

TABLE 3

| Component | Percentage by Volume |
| --- | --- |
| Pomace Olive Oil | 20.0% |
| Safflower Oil | 20.0% |
| Sweet Almond Oil | 10.0% |
| Apricot Kernel Oil | 10.0% |
| Avacado Oil | 10.0% |
| Jojoba Oil | 10.0% |
| Grape seed Oil | 10.0% |
| Sesame Oil | 10.0% |
| Tea Tree Oil | 0.05% |
| Rosemary Oleoresin Extract | 0.05% |
| Lemon Oil | 0.05% |
| Sweet Orange Oil | 0.05% |

It is to be understood that the aforementioned components and volumes disclosed in Table 3 are only exemplary and that various arrangements are possible in accordance with other exemplary embodiments of the cosmetic composition. The hair and body smoothing oil illustrated in Table 3 can have a total volume of approximately 20 ounces, although it is to be understood that the cosmetic composition can be provided in a variety of volumes in other embodiments.

One component of the cosmetic composition is safflower oil. This oil can be extracted from the seeds of the safflower plant. The oil is high in vitamin E and can impart this vitamin into the skin and hair of the user when employed. Also, safflower oil provides excellent moisturizing properties to the cosmetic composition so that the skin and hair, in turn, can be beneficially moisturized upon application.

The cosmetic composition shown in Table 3 also includes apricot kernel oil. This oil can be obtained through cold-pressing of the apricot kernel of the apricot plant. This oil is smooth in texture, lightweight, and is high in Vitamin A and minerals. Apricot kernel oil aids in improving aged skin and dry, irritated skin. Incorporation of apricot kernel oil into the cosmetic composition results in a hair and body smoothing oil that imparts moisturizing and softening benefits to the user. Additionally, apricot kernel oil functions as an absorption oil as it assists in absorption into the skin and hair of various components of the cosmetic composition.

Grape seed oil is also present in the cosmetic composition illustrated in Table 3. This oil is generally obtained through the pressing of grape seeds. The grape seed oil is typically light in weight and functions to thin out the texture of the cosmetic composition. Grape seed oil may function as a moisturizing oil in that it imparts beneficial moisturizing properties to the user when applied. Grape seed oil may also provide relief to stressed and damaged tissues and may impart regenerative qualities to the skin when applied. Grape seed oil may also function to reduce the appearance of stretch marks. This oil also provides for hair luster, manageability, and growth when applied to the hair of the user.

Sesame oil is additionally found in the cosmetic composition noted in Table 3. This oil is derived from sesame. Sesame oil is typically light and acts to thin out the texture of the resulting cosmetic composition. Sesame oil includes vitamins A and E and antioxidants that protect the hair and skin from sun and pollution damage.

Additional components of the hair and body smoothing oil are also included as shown in Table 3. These components have been previously described. Again, it is to be understood that the disclosed components and volumes are only exemplary and that other components may be added, subtracted, or substituted from the cosmetic composition when arranged as a hair and body smoothing oil. Additionally, the percentages by volume may be varied from those disclosed in Table 3.

In accordance with another exemplary embodiment of the present invention, the cosmetic composition can be formulated as a pomade useful in the styling of the hair of the user. The cosmetic composition is capable of being absorbed into the open follicles of a user's hair in order to restore luster thereto. The cosmetic product has been found to protect the hair of a user during heat styling. One embodiment of the cosmetic composition when formulated and used as a pomade is provided with reference to Table 4 below.

TABLE 4

| Component | Percentage by Volume |
| --- | --- |
| Petroleum Jelly | 15.4% |
| Pomace Olive Oil | 11.5% |
| Safflower Oil | 11.5% |
| Sweet Almond Oil | 11.5% |
| Coconut Oil | 11.5% |
| Cocoa Butter | 11.5% |
| Shea Butter | 11.5% |
| Jojoba Oil | 7.7% |
| Lanolin Butter | 7.7% |
| Tea Tree Oil | 0.05% |
| Rosemary Oleoresin Extract | 0.05% |
| Sweet Orange Oil | 0.05% |

In addition, an optional fragrance can be added such as vanilla fragrance oil. The volume of the resulting composition may be 0.05% vanilla fragrance oil when added. The components are provided so that the resulting texture is sufficient for use as a styling pomade. Again, it is to be understood that the aforementioned components and volumes disclosed in Table 4 are only exemplary and that various arrangements are possible in accordance with other exemplary embodiments of the cosmetic composition. The pomade illustrated in Table 4 can have a total volume of approximately 26 ounces, although it is to be understood that the cosmetic composition can be provided in a variety of volumes in other embodiments. Properties of the components listed in Table 4 have been previously discussed with respect to other exemplary embodiments and a repeat of the various components and their related properties is not necessary.

Another version of the pomade is presented below in Table 5.

TABLE 5

| Component | Percentage by Volume |
| --- | --- |
| Palm Kernel Oil | 33.3% |
| Petroleum Jelly | 16.7% |
| Pomace Olive Oil | 8.3% |
| Safflower Oil | 8.3% |
| Coconut Oil | 8.3% |
| Lanolin Butter | 8.3% |
| Palm Kernel Flakes | 8.3% |

TABLE 5-continued

| Component | Percentage by Volume |
| --- | --- |
| Beeswax | 8.3% |
| Sweet Orange Oil | 0.025% |

As with previous examples, it is to be understood that the aforementioned components and volumes disclosed in Table 5 are only exemplary and that various arrangements are possible in accordance with other exemplary embodiments of the cosmetic composition. The pomade illustrated in Table 5 can have a total volume of approximately 24 ounces, although it is to be understood that the cosmetic composition can be provided in a variety of volumes in other embodiments.

The cosmetic component illustrated in Table 5 includes palm kernel oil. This oil is extracted from the kernel of the palmfruit. This component adds texture to the resulting cosmetic composition. Palm kernel oil is also beneficial in providing moisturizing properties to the hair and scalp when applied.

Properties of the other components listed in Table 5 have been previously discussed with respect to other exemplary embodiments. Again, various components may be added, subtracted or substituted in different configurations. Further, the volume percentages provided are only exemplary and it is to be understood that other arrangements are possible.

An additional version of the cosmetic composition arranged as a pomade is presented in Table 6.

TABLE 6

| Component | Percentage by Volume |
| --- | --- |
| Petroleum Jelly | 25.0% |
| Pomace Olive Oil | 12.5% |
| Safflower Oil | 12.5% |
| Coconut Oil | 12.5% |
| Lanolin Butter | 12.5% |
| Palm Kernel Flakes | 12.5% |
| Beeswax | 12.5% |
| Sweet Orange Oil | 0.05% |

As with previous examples, it is to be understood that the aforementioned components and volumes disclosed in Table 6 are only exemplary and that various arrangements are possible in accordance with other exemplary embodiments of the cosmetic composition. The pomade illustrated in Table 6 can have a total volume of approximately 16 ounces, although it is to be understood that the cosmetic composition can be provided in a variety of volumes in other embodiments. The components have been previously described with respect to other configurations of the cosmetic composition. Another version of the cosmetic composition arranged as a pomade is presented in Table 7.

TABLE 7

| Component | Percentage by Volume |
| --- | --- |
| Sunflower Oil | 20.0% |
| Safflower Oil | 20.0% |
| Petroleum Jelly | 20.0% |
| Pomace Olive Oil | 10.0% |
| Sweet Almond Oil | 10.0% |
| Coconut Oil | 10.0% |
| Cocoa Butter | 10.0% |
| Tea Tree Oil | 0.05% |
| Rosemary Oleoresin Extract | 0.05% |
| Sweet Orange Oil | 0.05% |

In addition, an optional fragrance can be added. The option fragrance may be provided in vanilla fragrance oil and ylang-ylang fragrance oil. The volume of the resulting composition may be 0.05% of vanilla fragrance oil and 0.05% of ylang-ylang fragrance oil when added. The components are provided so that the resulting texture is sufficient for use as a styling pomade. Again, it is to be understood that the aforementioned components and volumes disclosed in Table 7 are only exemplary and that various arrangements are possible in accordance with other exemplary embodiments of the cosmetic composition. The pomade illustrated in Table 7 can have a total volume of approximately 20 ounces, although it is to be understood that the cosmetic composition can be provided in a variety of volumes in other embodiments.

One of the components of the version shown in Table 7 is sunflower oil. This oil is obtained from sunflower seeds and is rich in vitamin E and lecithin. Sunflower oil acts to retain moisture in the skin and may function as a barrier to prevent infection.

Properties of other components listed in Table 7 have been previously discussed with respect to other exemplary embodiments and a repeat of the various components and their related properties is not necessary.

Another version of the cosmetic composition arranged as a growth pomade is presented in Table 8.

TABLE 8

| Component |
| --- |
| Pomace Olive Oil |
| Grape Seed Oil |
| Sunflower Oil |
| Hemp Seed Oil |
| Emu Oil |
| Lanolin Butter |
| Petroleum Jelly |
| Tea Tree Oil |
| Peppermint Essential Oil |
| Clary-Sage Essential Oil |
| Lavender Essential Oil |
| Rosemary Oleoresin Extract |
| Sweet Orange Essential Oil |
| Ylang-Ylang Essential Oil |
| Coconut Oil |

In addition, an optional fragrance can be added. The optional fragrance may be provided in vanilla fragrance oil and ylang-ylang fragrance oil. The components are provided so that the resulting texture is sufficient for use as a growth pomade. The pomade may thus be used to style the hair of a user and promote hair growth. Again, it is to be understood that the aforementioned components disclosed in Table 8 are only exemplary and that various arrangements are possible in accordance with other exemplary embodiments of the cosmetic composition.

One of the components of the version shown in Table 8 is emu oil. This oil is obtained from refined fat of the emu bird and can provide medicinal benefits to the user. The coconut oil as disclose may be coconut oil or may be fractioned coconut oil or may be both coconut oil and fractioned coconut oil. The coconut oil employed may have a melt point of seventy six degrees Fahrenheit to help maintain a solid consistency and to help reduce the amount of petroleum jelly needed in the final product. Fractioned coconut oil is a liquid at room temperature and is more easily absorbed into the hair and skin. Properties of other various components listed in Table 8 have been previously discussed.

An additional exemplary embodiment of the cosmetic composition configured as an intense hair conditioner is presented in Table 9.

TABLE 9

| Component | Percentage by Volume |
| --- | --- |
| Water (hot when initially formed) | 34.0% |
| Conditioner pellets | 8.4% |
| Whole Egg Powder | 8.4% |
| Glycerine | 8.4% |
| Corn Starch-based Rheology Modifier and Emulsion Stabilizer | 6.3% |
| Pomace Olive Oil | 4.3% |
| Avacado Oil | 4.3% |
| Jojoba Oil | 4.3% |
| Soybean Oil | 4.3% |
| Castor Oil | 4.3% |
| Coconut Oil | 4.3% |
| Honey Powder | 1.4% |
| Goats Milk Powder | 1.4% |
| Hemp Seed Oil | 1.0% |
| Shea Oil | 1.0% |
| Wheat Protein | 1.0% |
| Rosemary Oleoresin Extract | 0.5% |
| Tea Tree Oil | 0.5% |
| Peppermint Oil | 0.5% |
| Clary Sage Oil | 0.5% |
| Lemongrass Oil | 0.5% |
| Ylang-ylang Oil | 0.5% |

In addition, an optional preservative can be added. The optional preservative may be GERMABEN® II-E which is provided in view of the egg and milk proteins present in the intense hair conditioner. GERMABEN® II-E is supplied by International Specialty Products having offices at 1361 Alps Road, Wayne, N.J., 07470. The components are provided so that the resulting texture is sufficient for use as a hair conditioner. Again, it is to be understood that the aforementioned components and volumes disclosed in Table 9 are only exemplary and that various arrangements are possible in accordance with other exemplary embodiments of the cosmetic composition. The intense hair conditioner illustrated in Table 9 can have a total volume of approximately 47.5 ounces, although it is to be understood that the cosmetic composition can be provided in a variety of volumes in other embodiments.

One of the components of the version shown in Table 9 are conditioner pellets. These pellets may be obtained from Soap Crafters, having offices at 2944 South West Temple, Salt Lake City, Utah, 84115. The conditioner pellets may contain palm oil derivatives in accordance with one exemplary embodiment.

Properties of certain other components listed in Table 9 have been previously discussed with respect to other exemplary embodiments and a repeat of the various components and their related properties is not necessary.

Another version of the cosmetic composition arranged as a clarifying facial mask is shown in Table 10.

TABLE 10

| Components |
| --- |
| Pomace Olive Oil |
| Safflower Oil |
| Jojoba Oil |
| Glycerine |
| Emulsifying Wax NF |
| Kaolin (Rose Clay) |
| Sea Clay |
| Bentonite Clay |

TABLE 10-continued

| Components |
|---|
| Lemon Powder |
| Honey Powder |
| Powdered Egg Whites |
| Tea Tree Oil |
| Lavender Oil |
| Water |
| Tea Tree and Willow Peel Off Face Mask Base |
| Coconut Oil |

In addition, an optional fragrance oil and/or a preservative can be added. The optional fragrance oil may be vanilla fragrance oil or ylang-ylang fragrance oil. The optional preservative can be GERMABEN® II-E. The components are provided so that the resulting texture is sufficient for use as a face mask. The clarifying facial mask can be applied to the face of the user and then removed after some amount of time in order to improve the look and feel of the user's skin. It is to be understood that the aforementioned components disclosed in Table 10 are only exemplary and that various arrangements are possible in accordance with other exemplary embodiments of the cosmetic composition.

The emulsifying Wax NF is provided in order to help hold the various oils of the clarifying facial mask together with the water. The kaolin (rose clay) functions to exfoliate the skin of the user. The sea clay may act to draw oils from the skin of the user, remove dead skin cells, and tighten the skin. The bentonite clay may act to help reduce the presence of acne on the face of the user. The tea tree willow peel off face mask base may be made from willow bark which may contain salicylic acid that together with the tea tree oil may help to reduce the presence of acne.

The coconut oil employed may be coconut oil, fractioned coconut oil, or a combination of coconut oil and fractioned coconut oil. Properties of certain other components listed in Table 10 have been previously discussed.

Another version of the cosmetic composition arranged as a hair and body milk is shown in Table 11.

TABLE 11

| Components |
|---|
| Pomace Olive Oil |
| Sesame Oil |
| Apricot Kernel Oil |
| Sweet Almond Oil |
| Avocado Oil |
| Jojoba Oil |
| Emu Oil |
| Castor Oil |
| Hemp Seed Oil |
| Soy Oil |
| Coconut Oil |
| Refined Lanolin Oil |
| Refined Shea Oil |
| Wheat Protein |
| Soy Protein |
| Honey Powder |
| Goats Milk Powder |
| Tea Tree Oil |
| Peppermint Oil |
| Lavender Oil |
| Ylang-ylang Oil |
| Lemongrass Oil |
| Clary-Sage Oil |
| Sweet Orange Oil |

TABLE 11-continued

| Components |
|---|
| Rosemary Oleoresin Extract |
| Glycerin |
| Water |

In addition, an optional fragrance oil and/or a preservative can be added. The optional fragrance oil may be vanilla fragrance oil. The optional preservative can be GERMABEN® II-E. The components are provided so that the resulting texture is sufficient for use as a hair and body milk. The hair and body milk can be applied to the skin or hair of the user in order to improve the look and feel and to impart soothing properties thereon. It is to be understood that the aforementioned components disclosed in Table 11 are only exemplary and that various arrangements are possible in accordance with other exemplary embodiments of the cosmetic composition.

Two of the components of the exemplary embodiment of Table 11 are refined lanolin oil and refined shea oil. The use of refined lanolin oil instead of lanolin oil may be beneficial in that greater moisturizing properties may be realized. However, it is to be understood that as used herein, the term shea oil is broad enough to include shea oil and/or refined shea oil. Further, as used herein the term lanolin oil is broad enough to encompass lanolin oil and/or refined lanolin oil. Properties of certain other components listed in Table 11 have been previously discussed.

An additional version of the cosmetic composition configured as a lip balm is illustrated in Table 12.

TABLE 12

| Components |
|---|
| Pomace Olive Oil |
| Olive Squalane |
| Safflower Oil |
| Castor Oil |
| Refined Jojoba Oil |
| Refined Lanolin Oil |
| Refined Shea Oil |
| Aloe Butter |
| Mango Butter |
| Honeyquat |
| Petroleum Jelly |
| Beeswax |
| Lemon Oil |
| Coconut Oil |

The components are provided so that the resulting texture has a consistency sufficient for use as a lip balm. The lip balm can be applied to the lips of the user in order to prevent drying and cracking during cold weather. It is to be understood that the aforementioned components disclosed in Table 12 are only exemplary and that various arrangements are possible in accordance with other exemplary embodiments of the cosmetic composition.

Refined jojoba oil is less oily and may have less odor than jojoba oil that is unrefined. However, it is to be understood that as used herein the term jojoba oil is broad enough to encompass jojoba oil and/or refined jojoba oil. The exemplary embodiment in table 12 includes olive squalane. This component is naturally derived from olive oil and is found in sebum which is a natural lubricant secreted by the skin of a user. Olive squalane provides properties to the resulting product so as to reduce its odor and make it less oily. Also, olive squalane aids in causing the resulting composition to more easily absorb into the skin of the user.

The coconut oil used can be coconut oil, fractioned coconut oil, or can be a combination of coconut oil and fractioned coconut oil. Properties of certain other components listed in Table 12 have been previously discussed.

Another exemplary embodiment of the cosmetic composition is disclosed in Table 13 and is an emulsion for users with normal skin conditions.

TABLE 13

| Components |
|---|
| Pomace Olive Oil |
| Olive Squalane |
| Emu Oil |
| Sweet Almond Oil |
| Refined Lanolin Oil |
| Refined Jojoba Oil |
| Refined Shea Oil |
| Sea Clay |
| Mango Butter |
| Cocoa Butter |
| Aloe Butter |
| Shea Butter |
| Honeyquat |
| Lemongrass Oil |
| Lemon Powder |
| Tea Tree Oil |
| Lavender Oil |
| Palm Kernel Flakes |

The components are provided so that the resulting texture has a consistency sufficient for use as a skin emulsion. The cosmetic component is specially formulated in this exemplary embodiment for use as a normal skin emulsion. The skin emulsion can be applied to the skin of users that do not have unusually dry or oily skin so that beneficial effects can be realized. It is to be understood that the aforementioned components disclosed in Table 13 are only exemplary and that various arrangements are possible in accordance with other exemplary embodiments of the cosmetic composition.

In accordance with a different exemplary embodiment, the sea clay can be substituted with bentonite clay. Also, it may be noted that refined jojoba oil, refined lanolin oil, and refined shea oil are present. Again, it is to be understood that as used herein the terms lanolin oil, jojoba oil, and shea oil are broad enough to encompass their refined and/or unrefined forms.

The coconut oil used may be coconut oil, fractioned coconut oil, or a combination of coconut oil and fractioned coconut oil. Properties of various components disclosed in Table 13 have been discussed in accordance with other exemplary embodiments.

Another exemplary embodiment of the cosmetic composition is disclosed in Table 14 and is a warming emulsion.

TABLE 14

| Components |
|---|
| Pomace Olive Oil |
| Castor Oil |
| Jojoba Oil |
| Lanolin Butter |
| Aloe Butter |
| Shea Butter |
| Eucalyptus Oil |
| Wintergreen Oil |
| Tea Tree Oil |
| Menthol Crystals |
| Petroleum Jelly |
| Evening Primrose Oil |
| Peppermint Oil |

The components are provided so that the resulting texture has a consistency sufficient for application to the skin of a user for use as a warming emulsion. The warming emulsion can be used for warming, soothing, and healing purposes by the user. Additionally, the warming emulsion may prove helpful in relieving muscle aches and pains, and the warming emulsion can be used in the treatment of colds and flu. It is to be understood that the aforementioned components disclosed in Table 14 are only exemplary and that various arrangements are possible in accordance with other exemplary embodiments of the cosmetic composition.

One component of the cosmetic composition in Table 14 are menthol crystals. These crystals provide a pleasing, minty aroma to the resulting composition. The menthol crystals may need to be heated in order to melt so that they can be mixed into the other various components. In this regard, all of the components may be heated in order to integrate the menthol crystals, or only a portion of the components may be heated. Further, the menthol crystals can be heated separately and then mixed with the other various components of the cosmetic composition. The menthol crystals are made through mint essential oil extraction and can function to relive muscle aches and pains of the user in addition to providing relief from colds and congestion.

Evening primrose oil is also included in the cosmetic composition shown in Table 14. This oil is extracted from the seeds of the evening primrose plant. Evening primrose oil is beneficial in treating rheumatoid arthritis and may impart this functionality to the cosmetic composition when incorporated therein.

Properties of other components disclosed in Table 14 have been discussed in accordance with other exemplary embodiments.

As previously mentioned, the cosmetic composition as disclosed in the tables are only exemplary, and it is to be understood that other arrangements of the cosmetic composition exist. For instance, certain components in the exemplary embodiment of Table 1 may be replaced with certain components in the exemplary embodiment of Table 2 to yield a different version of the cosmetic component. All of the cosmetic components include olive oil. The olive oil may be pomace olive oil in accordance with various exemplary embodiments. From 5% to 25% of the cosmetic composition may be made of pomace olive oil by volume. Other arrangements are possible in which up to 27%, up to 32%, and up to 40% by volume of pomace olive oil is present in the cosmetic composition. Further, from 10% to 20%, from 15% to 22%, from 7.2% to 20%, or from 12% to 30% by volume of pomace olive oil may be included in various versions of the cosmetic composition.

Additionally, other oils as those presented may be incorporated into the cosmetic composition with the pomace olive oil. It is to be understood that the oils listed, such as but not limited to lemongrass oil, ylang-ylang oil, clary-sage oil, sweet orange oil and peppermint oil may be essential oils. As such, it is to be understood as used herein and in the claims that the listed oils may also be essential oils. Exemplary embodiments may include only one oil in addition to the pomace olive oil, or may include two oils in addition to the pomace olive oil. Other exemplary embodiments exist in which from three to six of the previously mentioned oils, in addition to the pomace olive oil, are present in the cosmetic composition. The additional components may or may not be provided in accordance with various exemplary embodiments.

The cosmetic compositions described herein may be chemical free such that a chemical is not included as one of the components of the cosmetic composition. Additionally, the components of the cosmetic compositions may be all natural. Various oils described may be close to the body's natural oils. This feature allows the cosmetic composition and their component oils to be more readily absorbed into the skin and hair of the user. The cosmetic compositions may be designed so that mineral oil is not included as a component. Further, exemplary embodiments exist in which water is not included as a component. However, in accordance with other versions, water may be added as a component of the cosmetic composition. In order to create the cosmetic compositions, the various components may be measured out into a cup and then mixed together. Heating the resulting mixture may or may not be performed.

Although described in the claims as being a moisturizing oil, absorption oil, bacterial control oil, vitamin rich oil, hydrophobic agent, or texturing agent, it is to be understood that the various components may perform one or more of these functions and that the particular component is not to be limited to just the one identified function. As such, the identified component can perform the identified function in addition to other non-identified functions. The description is to be understood as being made for the sake of convenience.

While described as being capable of including one or more of the presented oils, it is to be understood that other arrangements exist in which only one of the listed oils, in addition to pomace olive oil, is present in the cosmetic composition. Further, in accordance with other exemplary embodiments, only two of the listed oils are present, in addition to pomace olive oil. In yet other arrangements, only three of the listed oils are present, in addition to pomace olive oil. In yet other exemplary embodiments, only four of the listed oils are present, in addition to pomace olive oil.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A cosmetic emulsion consisting of:
pomace olive oil;
castor oil;
jojoba oil;
lanolin butter;
aloe butter;
shea butter;
eucalyptus oil;
wintergreen oil;
tea tree oil;
menthol crystals;
petroleum jelly;
evening primrose oil; and
peppermint oil;
wherein the pomace olive oil, the castor oil, the jojoba oil, the lanolin butter, the aloe butter, the shea butter, the eucalyptus oil, the wintergreen oil, the tea tree oil, the menthol crystals, the petroleum jelly, the evening primrose oil, and the peppermint oil are combined with one another in a mixture together and the mixture is a warming emulsion.

2. A cosmetic emulsion consisting of:
pomace olive oil;
sweet almond oil;
jojoba oil;
mango butter;
aloe butter;
cocoa butter;
shea butter;
coconut oil;
palm kernal flakes;
beeswax;
lanolin butter;
petroleum jelly;
sweet orange oil; and
lemon oil;
wherein the pomace olive oil, the sweet almond oil, the jojoba oil, the mango butter, the aloe butter, the cocoa butter, the shea butter, the coconut oil, the palm kernal flakes, the beeswax, the lanolin butter, the petroleum jelly, the sweet orange oil, and the lemon oil are combined with one another in a mixture together and the mixture is a dry skin emulsion.

3. A cosmetic emulsion consisting of:
petroleum jelly;
pomace olive oil;
safflower oil;
sweet almond oil;
coconut oil;
cocoa butter;
shea butter;
jojoba oil;
lanolin butter;
tea tree oil;
rosemary oleoresin extract; and
sweet orange oil;
wherein the petroleum jelly, the pomace olive oil, the safflower oil, the sweet almond oil, the coconut oil, the cocoa butter, the shea butter, the jojoba oil, the lanolin butter, the tea tree oil, the rosemary oleoresin extract, and the sweet orange oil are combined with one another in a mixture together.

4. A cosmetic emulsion consisting of:
water;
conditioner pellets;
whole egg powder;
glycerine;
corn starch-based rheology modifier and emulsion stabilizer;
pomace olive oil;
avacado oil;
jojoba oil;
soybean oil;
castor oil;
coconut oil;
honey powder;
goats milk powder;
hemp seed oil;
shea oil;
wheat protein;
rosemary oleoresin extract;
tea tree oil;
peppermint oil;
clary sage oil;
lemongrass oil; and
ylang-ylang oil;
wherein the water, the conditioner pellets, the whole egg powder, the glycerine, the corn starch-based rheology modifier and emulsion stabilizer, the pomace olive oil, the avacado oil, the jojoba oil, the soybean oil, the castor oil, the coconut oil, the honey powder, the goats milk powder, the hemp seed oil, the shea oil, the wheat protein, the rosemary oleoresin extract, the tea tree oil, the peppermint oil, the clary sage oil, the lemongrass oil, and the ylang-ylang oil are combined with one another in a mixture together.

* * * * *